United States Patent [19]

Stella et al.

[11] 4,260,769
[45] Apr. 7, 1981

[54] 5,5-DIPHENYLHYDANTOINS

[75] Inventors: Valentino J. Stella, Lawrence; Kenneth B. Sloan, Eudora, both of Kans.

[73] Assignee: INTERx Research Corporation, Lawrence, Kans.

[21] Appl. No.: 33,234

[22] Filed: Apr. 25, 1979

Related U.S. Application Data

[62] Division of Ser. No. 790,087, Apr. 22, 1977, Pat. No. 4,163,058.

[51] Int. Cl.³ .................................. C07F 9/06
[52] U.S. Cl. ...................................... 548/112
[58] Field of Search .......................... 548/312, 112

[56] References Cited

U.S. PATENT DOCUMENTS

| | | | |
|---|---|---|---|
| 2,928,841 | 3/1960 | McConnell et al. | 548/312 |
| 3,676,454 | 7/1972 | Vida | 548/312 |
| 3,741,978 | 6/1973 | Jamison | 548/112 |
| 3,835,151 | 9/1974 | Havera et al. | 548/312 |
| 3,920,686 | 11/1975 | Samour | 548/312 |
| 3,946,034 | 3/1976 | Porret et al. | 548/312 |
| 4,163,058 | 7/1979 | Stella et al. | 548/312 |

FOREIGN PATENT DOCUMENTS

| | | | |
|---|---|---|---|
| 2064474 | 7/1971 | Fed. Rep. of Germany | 548/312 |
| 1093728 | 5/1955 | France | 548/312 |

Primary Examiner—John D. Randolph
Assistant Examiner—Jane T. Fan
Attorney, Agent, or Firm—Burns, Doane, Swecker & Mathis

[57] ABSTRACT

Novel 5,5-diphenylhydantoins useful as anticonvulsants, antiepileptics and antiarrhythmics have the structural formula:

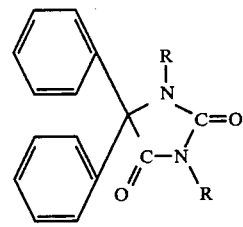

wherein each R is hydrogen or —CH($R_1$)—X—P(O)-(OH)$_2$, $R_1$ is hydrogen or $C_1$–$C_7$ straight or branched chain alkyl, and X is O or S, with the proviso that both R's cannot simultaneously be hydrogen.

3 Claims, No Drawings

5,5-DIPHENYLHYDANTOINS

This is a division of application Ser. No. 790,087, filed Apr. 22, 1977, now U.S. Pat. No. 4,163,058.

BACKGROUND OF THE INVENTION

1. Field of the Invention

The present invention relates to novel and therapeutically useful derivatives of phenytoin. More particularly, the present invention concerns the discovery of a group of novel derivatives of phenytoin which offer enhanced solubility over phenytoin per se.

These compounds are extremely useful as anticonvulsants, antiepileptics and antiarrhythmics and can be administered to warm-blooded animals (e.g., humans) per se or in pharmaceutical composition form when admixed with a suitable nontoxic pharmaceutically acceptable carrier.

2. Description of the Prior Art

A pharmaceutical and medical need exists for new and useful compounds indicated from the management of epilepsy and other types of convulsive states, and cardiac arrythmics. The need exists because compounds such as 5,5-diphenylhydantoin, generally referred to as diphenylhydantoin or phenytoin, which is most commonly and widely used for the treatment of these conditions possess extremely low solubility and hence, low bioavailability per se as well as from pharmaceutical dosage forms. For example, 5,5-diphenylhydantoin which has a therapeutic index between 1 and 2, a pKa of 8.3, and a solubility of less than 2 mg. in 100 ml at 37° C. often produces unpredictable and erractic release patterns, both in vitro and in vivo. Also, when 5,5-diphenylhydantoin is orally administered in the form of its sodium salt, it frequently causes gastric irritation due to the alkalinity of the administered dosage form. For intravenous administration, sodium 5,5-diphenylhydantoin is generally used in a formulation comprising 40% propylene glycol and 10% alcohol in water, adjusted with sodium hydroxide to a high alkaline pH. Intravenous administration of this formulation frequently leads to precipitation of 5,5-diphenylhydantoin as well as erractic blood levels. Intramuscular use of sodium 5,5-diphenylhydantoin has been shown to precipitate 5,5-diphenylhydantoin at the injection site leading to delayed and erractic 5,5-diphenylhydantoin release. Other hydantoins have similar problems to those seen with 5,5-diphenylhydantoin. This common and wide use of the hydantoins with their accompanying disadvantages, and specifically, their low solubilities, creates an immediate and pressing need for new and useful pharmaceutical compounds that possess therapeutic properties useful for treating epilepsy and other convulsive states, and cardiac arrythmics, while remaining essentially free from the unwanted effects associated with the prior art compounds.

U.S. Pat. No. 3,595,862 claims the potential usefulness of N,N'-bis(acyloxymethyl)5,5-diphenylhydantoin compounds as effective anticonvulsants. The compounds of this patent include those in which the acyloxy groups are acetoxy, acryloxy, methacryloyloxy, propionoxy and benzoyloxy. The compounds are inferior in solubility to the compounds claimed in this application and in fact have solubility characteristics similar to 5,5-diphenylhydantoin itself.

SUMMARY OF THE INVENTION

Accordingly, it is an immediate object of this invention to provide novel pharmaceutical compounds that are useful as antiepileptics, anticonvulsants and antiarrythmics.

Another object of this invention is to provide novel and useful derivatives of diphenylhydantoin which are characterized as being substantially more soluble than the parent specie per se.

Still, another object of this invention is to provide novel and useful derivatives of diphenylhydantoin which, in addition to exhibiting enhanced solubility, are essentially free from the unwanted effects associated with the physical and chemical properties of prior art derivatives.

Finally, another object of the present invention is to provide new and useful derivatives of diphenylhydantoin as characterized above which further exhibit enhanced stability such that they can be tolerated in conventional pharmaceutical dosage formulations.

All the foregoing objects are achieved by administering to a warm-blooded animal in need of anticonvulsants and/or antiepileptic therapy, a compound having the formula:

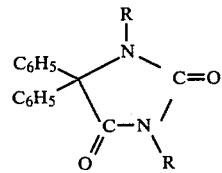

wherein R represents H or a member selected from the group consisting of

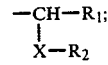

wherein $R_1$ represents a member selected from the group consisting of H, $C_1$-$C_7$ straight or branched alkyl,

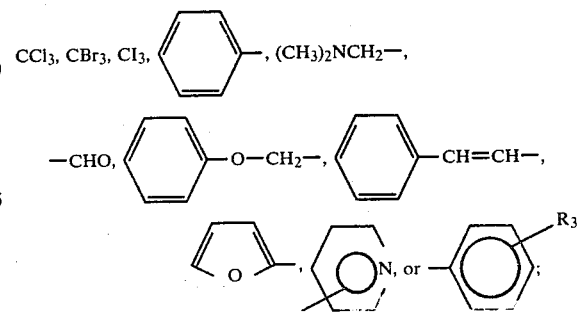

wherein $R_3$ represents a member selected from the group consisting of —OH, halogen (Cl, Br, I), —OCH$_3$, —COOCH$_3$, —NO$_2$ or —OCOCH$_3$; wherein X is -

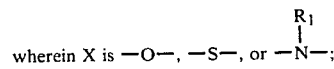

and wherein $R_2$ represents a member selected from the group consisting of

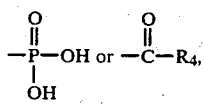

wherein $R_4$ is a member selected from the group consisting of

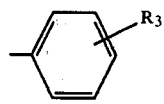

wherein $R_3$ is defined as above,

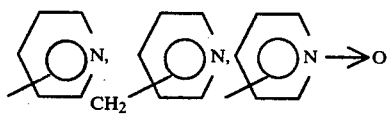

the residue of any naturally occurring protein amino acid, the residue of any N- substituted amino acid, wherein said substituent is any amino acid protective group cleavable via hydrogenolysis of hydrolysis (e.g., formyl, benzyloxy, carbonyl, t-butyloxycarbonyl) or the residue of an $N,N-C_1-C_5$—dialkyl or $C_4-C_7$ cycloalkylamino acid, or wherein $R_4$ is a member selected from the group consisting of

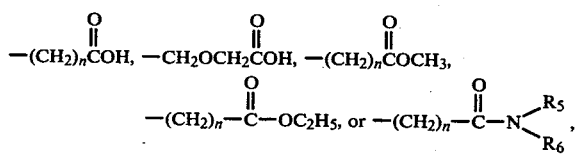

wherein n represents an integer of from 1–5 and $R_5$ and $R_6$ which may be the same or different represent $C_1-C_5$ alkyl or together form a heterocyclic ring with the N atom to which they are attached (e.g., pyrolidine, piperidine, morpholine, piperazine, imidazoline, thiazolidine), or wherein $R_4$ is a member selected from the group consisting of imidazolyl, $-O-C_1-C_8$ alkyl, —O—benzyl, —O—phenyl, and

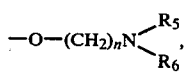

wherein n, $R_5$ and $R_6$ are defined as above; with the proviso that R in both occurrences cannot represent H simultaneously; or the pharmaceutically acceptable acid addition or basic salts, $C_1-C_4$ alkylhalide quaternary salts or N-oxide thereof. ;p While all the compounds encompassed within the above generic formula suffice for the applicants' purposes, nevertheless, certain selected compounds are preferred as noted below. A "most" preferred group of compounds is claimed hereinafter.

1. 3-Ethoxycarbonyloxymethyl-diphenylhydantoin.
2. 3-Benzyloxycarbonyloxymethyl-diphenylhydantoin.
3. 3-(2′,2′,2′-Trichloroethyloxycarbonyloxymethyl)-diphenylhydantoin.
4. 3-(N,N-Dimethylglycyloxymethyl)-diphenylhydantoin.
5. 3-(1-Piperidylacetyloxymethyl)-diphenylhydantoin.
6. 3-Benzoyloxymethyl-diphenylhydantoin.
7. 3-p-Toluyloxymethyl-diphenylhydantoin.
8. 3-Picolinoyloxymethyl-diphenylhydantoin.
9. 3-Nicotinoyloxymethyl-diphenylhydantoin.
10. 3-N-Formylglycyloxymethyl-diphenylhydantoin.
11. 3-Glycyloxymethyl-diphenylhydantoin.
12. 3-N-Benzyloxycarbonylglycyloxymethyl-diphenylhydantoin.
13. 3-Methylsuccinyloxymethyl-diphenylhydantoin.
14. 3-(N,N-Dimethylsuccinamyloxymethyl)-diphenylhydantoin.
15. 3-(N,N-Diethylsuccinamyloxymethyl)-diphenylhydantoin.
16. 3-(N,N,N-Trimethylglycyloxymethyl)-diphenylhydantoin.
17. 3-(N,N,N-Triethylglycyloxymethyl)-diphenylhydantoin.
18. 3-[α-(N,N-Dimethylglycyloxy)ethyl]-diphenylhydantoin.
19. 3-[α-(1-Piperidylacetyloxy)ethyl]-diphenylhydantoin.
20. 3-(α-Benzoyloxyethyl)-diphenylhydantoin.
21. 3-(α-Picolinoyloxyethyl)-diphenylhydantoin.
22. 3-[α-(N-Formylglycyloxy)ethyl]-diphenylhydantoin.
23. 3-[α-(N-Benzyloxycarbonylglycyloxy)ethyl]-diphenylhydantoin.
24. 3-(α-Methylsuccinyloxyethyl)-diphenylhydantoin.
25. 3-[α-(N,N-Dimethylsuccinamyloxy)ethyl]-diphenylhydantoin.
26. 3-[α-(N,N,N-Trimethylglylcyloxy)ethyl]-diphenylhydantoin chloride.
27. 3-(α-Ethoxycarbonyloxybenzyl)-diphenylhydantoin.
28. 3-[α-(N,N-Dimethylglycyloxy)benzyl]-diphenylhydantoin.
29. 3-[α-(1-Piperidylacetyloxy)benzyl]-diphenylhydantoin.
30. 3-(α-Picolinoyloxybenzyl)-diphenylhydantoin.
31. 3-[α-(N-Formylglycycloxy)benzyl]-diphenylhydantoin.
32. 3-[α-(N-Benzyloxycarbonylglycyloxy)benzyl]-diphenylhydantoin.
33. 3-(α-Methylsuccinyloxybenzyl)-diphenylhydantoin.
34. 3-[α-(N,N-Dimethylsuccinamyloxy)benzyl]-diphenylhydantoin.
35. 3-[α-(N,N,N-Trimethylglycyloxy)benzyl]-diphenylhydantoin chloride.
36. 3-(N,N-Dimethylglycylthiomethyl)-diphenylhydantoin.
37. 3-(1-Piperidylacetylthiomethyl)-diphenylhydantoin.
38. 3-p-Toluylthiomethyl-diphenylhydantoin.
39. 3-Picolinoylthiomethyl-diphenylhydantoin.
40. 3-Nicotinoylthiomethyl-diphenylhydantoin.
41. 3-N-Formylglycylthiomethyl-diphenylhydantoin.
42. 3-Glcylthiomethyl-diphenylhydantoin.
43. 3-(N,N-Diethylsuccinamylthiomethyl)-diphenylhydantoin.
44. 3-(N,N,N-Trimethylglycylthiomethyl)-diphenylhydantoin chloride.
45. 3-(N,N,N-Triethylglycylthiomethyl)-diphenylhydantoin chloride.
46. 3-Phosphoryloxymethyl-diphenylhydantoin.
47. 3-Succinyloxymethyl-diphenylhydantoin.
48. 3-Glutaryloxymethyl-diphenylhydantoin.

A "most preferred" group of compounds are claimed hereinafter.

The phrase "non-toxic . . . addition salts" as used herein generally includes the non-toxic acid or basic addition salts of the compounds within the above-described generic formula, formed with non-toxic inorganic and organic acids or bases. For example, the former salts include those derived from inorganic acid such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicyclic, sulfanilic, fumaric, toluenesulfonic, methanesulfonate, and the like. The latter salts include those derived from alkali or alkaline earth metal bases or conventional organic bases, e.g., triethylamine, pyridine, piperidine, morpholine, N-methylmorpholine, etc.

The term "naturally occurring protein amino acid" includes without limitation:

| | |
|---|---|
| Glycine | Arginine |
| Alanine | Lysine |
| Valine | Hydroxylsine |
| Leucine | Phenylalanine |
| Isoleucine | Tyrosine |
| Cysteine | Asparagine |
| Cystine | Glutamine |
| Methionine | Proline |
| Serine | Hydroxyproline |
| Threonine | Histidine |
| Aspartic acid | Tryptophan |
| Glutamic acid | Pyroglutamic acid |

Similarly, the import of the phrase "amino acid protective group 'cleavable' via hydrogenolysis or hydrolysis" can be further gained from a review of U.S. Pat. No. 3,803,120—Felix and U.S. Pat. No. 3,957,803—Bodor, et al.

All the compounds within generic formula (I) are prepared by way of reaction schemes (I) or (II) set out below, wherein R, $R_1$, $R_2$ and $R_4$ are defined as above; and wherein X represents an oxygen, sulfur or nitrogen atom, M represents an alkali or alkaline earth metal (Na, K, Ca, Mg) or thallium, and wherein Y represents a halogen atom, e.g., F, Cl, Br or I. Unless otherwise stated, all reactants are employed in stoichiometric amounts and all reactions are run at standard temperature and pressure.

Reaction Scheme (I)

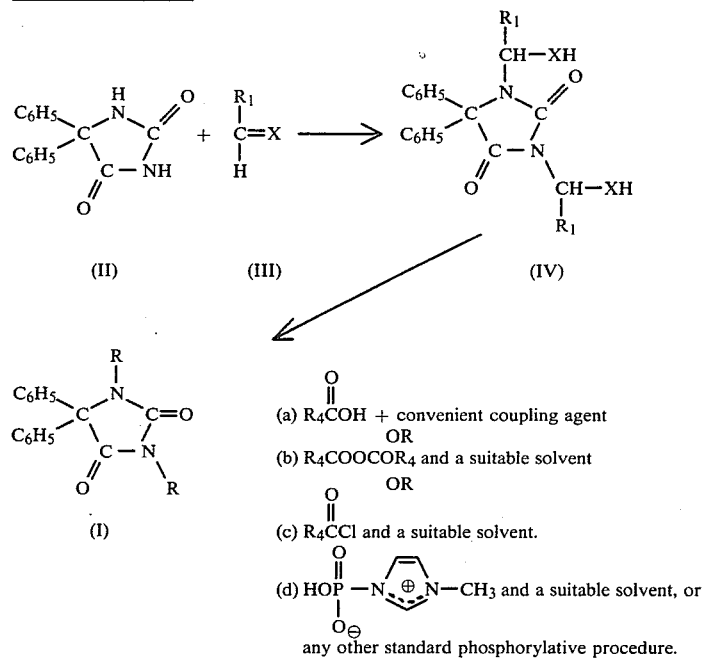

Reaction Scheme (II)

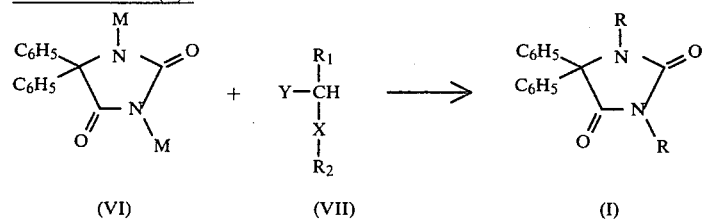

In reaction scheme (I), the use of a solvent is optional. When desired, however, water is sufficient. When using a coupling agent in the final step of converting the compound of formula (IV) to the final compound of formula (I), any suitable conventional organic coupling agent can be employed. Illustrative of such agents are DCCI or EEDQ. Additional coupling agents can be ascertained from the text entitled CHEMISTRY OF AMINO ACIDS (1964), McGraw-Hill. Finally, the reaction for scheme (I) is run at standard temperature and pressure, over a period of from one to 24 hours.

With respect to reaction scheme (II), the reaction is run in a solvent comprising any suitable organic material such as dimethylformamide, ether, halogenated hydrocarbon, etc. The reaction is normally run over a period of from one to 24 hours at standard pressure and at a temperature ranging from room temperature to the boiling point of the solvents selected.

When using either reaction scheme, the final compound of formula (I) can be obtained via standard crystallization procedures, and if necessary, recrystallization can be carried out in the presence of any suitable organic solvent.

In reference to reaction scheme (I), the intermediate compound of formula (IV) is also deemed novel by the applicant, and accordingly, is claimed hereinafter.

The non-toxic pharmaceutically acceptable acid addition salts or acceptable basic salts $C_1$–$C_4$ quaternary alkylhalides or N-oxidesof the present invention can be synthesized from the compounds embraced by formula (I) by conventional chemical methods. Normally, the salts are prepared by reacting the free base or acid with stoichiometric amounts or with an excess thereof of the desired salt forming inorganic or organic acid or base in a suitable solvent or various combination of solvents. As an example, the free base or acid can be dissolved in an aqueous solution of the appropriate acid or base and the salt recovered by standard techniques, for example, by evaporation of the solution. Alternatively, the free base or acid can be dissolved in an organic solvent such as a lower alkanoyl, an ether, an alkyl ester, or mixtures thereof, for example, methanol, ethanol, ether, ethylacetate, an ethylacetate-ether solution, and the like, whereafter it is treated with the appropriate acid or base to form the corresponding salt. The salt is recovered by standard recovery techniques, for example, by filtration of the desired salt on spontaneous separation from the solution, or it can be precipitated by the addition of a solvent in which the salt is insoluble and recovered therefrom.

The quaternary alkylhalides and N-oxides are prepared in similar fashion by reacting the compound of formula of formula (I) with the corresponding alkylhalide or N-oxide.

Without further elaboration, it is believed that one of ordinary skill in the art can, using the preceding description, utilize the present invention to its fullest extent. Accordingly, the following preferred specific embodiments are, therefore, to be construed as merely illustrative and not limitative of the remainder of the specification and claims in any way whatsoever.

PREPARATION OF THE 3-(HYDROXYMETHYL)DIPHENYLHYDANTOIN PRECURSOR 20 g of 5,5-diphenylhydantoin (0.08 moles) and 80 ml (32 g) of formalin are introduced into a suitable reaction vessel containing 720 ml of water and one g of potassium carbonate. The reaction is stirred at room temperature for 24 hours, after which the subject compound, mp 186.5°–188.5° C., yield 22.58 g (91.86%) is obtained by filtration.

EXAMPLE I-PREPARATION OF SOME SELECTED COMPOUNDS OF FORMULA (I)

PREPARATION OF 3-(N,N-DIMETHYLGLYCYLOXYMETHYL)DIPHENYLHYDANTOIN

Into a suitable reaction vessel containing 5 ml of pyridine, there is added one g (0.0035 mols) of 3-hydroxymethyl-diphenylhydantoin, 0.36 g (0.0035 mols) of N,N-dimethylglycine and 0.79 g (0.0035 mols) of dicyclohexylcarbodiimide (DCCI). The reaction mixture is stirred at room temperature for a period of approximately 24 hours, after which the final product, mp 128°–130°, yield 0.86 g (66.7%) is obtained.

PREPARATION OF 3-(N,N-DIMETHYGLYCYLOXYMETHYL)DIPHENYLHYDANTOIN METHANESULFONATE

Into a suitable reaction vessel containing a sufficient amount of dichloromethane ($CH_2Cl_2$), there was introduced 0.310 g (0.0032 mols) of methylsulfonic acid ($CH_3SO_3H$) and 1.18 g (0.0032 mols) of N,N-dimethylglycyloxymethyl-diphenylhydantoin. The reaction mixture was stirred at room temperature overnight after which the subject compound, mp 173°–175° C., yield 2.25 g (92.6%) was obtained.

PREPARATION OF 3-(N,N-DIMETHYLGLYCYLOXYMETHYL)DIPHENYLHYDANTOIN SALICYLATE

By following the immediately preceding reaction scheme but substituting a stoichiometric amount of salicyclic acid for methysulfonic acid, the subject compound was obtained in quantatative yield.

PREPARATION OF 3-(GLUTARYLOXYMETHYL)DIPHENYLHYDANTOIN

To a suitable reaction vessel containing 25 ml of pyridine, there was added 10 g (0.0354 mols) of 3-hydroxymethyldiphenyldydantoin and 4.85 g (0.0425 mols) of glutaric anhydride. The reaction mixture was stirred at room temperature for 5 days, thus obtaining the subject compound, mp 137.5°–146° C., yield 7.90 g (56.0%).

PREPARATION OF 3-(SUCCINYLOXYMETHYL)DIPHENYLHYDANTOIN

To a suitable reaction vessel containing 25 ml of pyridine, there was added 10 g (0.0354 mols) of 3-hydroxymethyldiphenylhydantoin and 4.25 g (0.0425 mols) of succinyl anhydride. The reaction mixture was stirred at room temperature for 5 days after which the subject compound, mp 141.5°–146° C. yield 8.36 g (62.0%) was obtained.

In similar fashion, the remaining compounds of the present invention can be prepared with similar success by merely following the preceding examples and substituting the generically and/or specifically described reactants and/or operating conditions of this invention for those of the preceding examples.

The improved solubility of the novel compounds of the instant invention is demonstrated via 3-(N,N-dimethylglycyloxymethyl)diphenylhydantoin methanesulfonate, a selective compound from within formula (I). The compound was added in increments to water until solubility was determined. The solubility for the subject compound was in excess of 100 mg/ml which is quite dramatic when compared to the solubility of the parent scale, diphenylhydantoin per se, i.e., less than 0.02 mg/ml (approximate 5,000 fold increase in aqueous solubility over diphenylhydantoin).

When repeating the above-described solubility experiment, but this time, employing the remaining compounds of formula (I), substantially improved solubility characteristics over diphenylhydantoin are observed.

The novel and useful diphenylhydantoin compounds of this invention can be used by the pharmaceutical and the veterinary arts for their antiepileptic, anticonvulsant and antiarrhythmic effects in a variety of pharmaceutical or veterinary preparations In these preparations, the new compounds are administrable in the form of tablets, pills, powder mixtures, capsules, injectables, solutions, suppositories, emulsions, dispersions, food premix, and in other suitable form. The pharmaceutical or veterinary preparation which contains the compound is conveniently admixed with a nontoxic pharmaceutical organic carrier or a nontoxic pharmaceutical inorganic carrier, usually about 0.01 mg up to 2500 mg, or higher per dosage unit. Typical of pharmaceutically acceptable carriers are, for example, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like, as for example, sorbitan monolaurate, triethanolamine oleate, polyoxyethylene monostearate, glyceryl tripalmitate, dioctyl sodium sulfosuccinate, and the like.

Exemplary of a typical method for preparing a tablet containing the active agents is to first mix the agent with a nontoxic binder such as gelatin, acacia mucilage, ethyl cellulose, or the like. The mixing is suitably carried out in a standard V-blender and usually under anhydrous conditions. Next, the just prepared mixture can be slugged through conventional tablet machines and the slugs fabricated into tablets. The freshly prepared tablets can be coated, or they can be left uncoated. Representative of suitable coatings are the nontoxic coatings including shellac, methylcellulose, carnauba wax, styrene-maleic acid copolymers, and the like. For oral administration, compressed tablets containing 0.01 milligram, 5 milligrams, 25 milligram, 50 milligrams, etc., up to 2500 milligrams are manufactured in the light of the above disclosure and by art known fabrication techniques well known to the art and set forth in Remington's Pharmaceutical Science, Chapter 39, Mack Publishing Co., 1965. The pharmaceutical manufacture of a formulation is shown in Example II.

EXAMPLE II

| Ingredients: | Per tablet, mg. |
| --- | --- |
| 3-(N,N-dimethylglycyloxymethyl)-diphenylhydantoin methanesulfonate | 50.0 |
| Cornstarch | 15.0 |
| Cornstarch paste | 4.5 |
| Calcium carbonate | 15.0 |
| Lactose | 67.0 |
| Calcium stearate | 2.0 |

-continued

| Ingredients: | Per tablet, mg. |
| --- | --- |
| Dicalcium phosphate | 50.0 |

To formulate the tablet uniformly blend the active compound, cornstarch, lactose, dicalcium phosphate and calcium carbonate under dry conditions in a conventional V-blender until all the ingredients are uniformly mixed together. Next, the cornstarch paste is prepared as a 10% paste and it is blended with the just prepared mixture until a uniform mixture is obtained. The mixture is then passed through a standard light mesh screen, dried in an anhydrous atmosphere and then blended with calcium stearate, and compressed into tablets, and coated if desired. Other tablets containing 10, 50, 100, 150 mgs, etc., are prepared in a like fashion.

EXAMPLE III

| Ingredients: | Per tablet, mg. |
| --- | --- |
| 3-(N,N-dimethylglycyloxymethyl)diphenylhydantoin methanesulfonate | 50.0 |
| Cornstarch | 15.0 |
| Cornstarch paste | 4.5 |
| Calcium carbonate | 15.0 |
| Lactose | 67.0 |
| Calcium stearate | 2.0 |
| Dicalcium phosphate | 50.0 |

The manufacture of capsules containing 10 milligrams to 2500 milligrams for oral use consists essentially of mixing the active compound with a nontoxic carrier and enclosing the mixture in a polymeric sheath, usually gelatin or the like. The capsules can be in the art known soft form of a capsule made by enclosing the compound in intimate dispersion within an edible, compatible carrier, or the capsule can be a hard capsule consisting essentially of the novel compound mixed with a nontoxic solid such as talc, calcium stearate, calcium carbonate, or the like. Exemplary of a typical use for employing a capsule containing 100 mg of 3-(N,N-dimethylglycyloxymethyl)diphenylhydantoin methanesulfonate for use as therapeutically indicated ad libitum for antiepileptic effects. Capsules containing 25 mg, 75 mg, 125 mg, and the like, of the novel compounds, singularly or mixtures of two or more of the novel compounds are prepared, for example, as follows:

EXAMPLE IV

| Ingredients: | Per capsule, mg. |
| --- | --- |
| Active compound of formula (I) | 50.0 |
| Calcium carbonate | 100.0 |
| Lactose, U.S.P. | 200.0 |
| Starch | 130.0 |
| Magnesium stearate | 4.5 |

The above ingredients are blended together in a standard blender and then discharged into commercially available capsules. When higher concentrations of the active agent is used, a corresponding reduction is made in the amount of lactose.

The dose administered, whether a single dose, multiple dose, or a daily dose, will of course, vary with the particular compound of the invention employed because of the varying potency of the compound, the chosen route of administration, the size of the recipient and the nature of the arrythmia or epileptic seizure and other states characterized by involuntary movements such as Parkinson's syndrome. The dosage administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage administered for the management of cardiac arrythmias, grand mal, petit mal, psychomoter equivalent seizures and other forms of convulsive seizures is for mammals, including primates and humans a general oral dose of 200 to 300 mg daily, with the oral dose of normally 100 mg up to 4 times a day; the usual intravenous dose of 100 to 350 mg, followed by if indicated 100 to 150 mg at a later period, and the usual intramuscular dose of 100 to 300 mg every 6 to 8 hours, with 3 to 4 injections per day. For household animals, such as dogs, the administrable dose is about 30 to 200 mg about every 6 to 8 hours.

For administering to valuable household animals, such as dogs, or for administering to laboratory animals such as mice, for scientific studies, the compound is prepared in the form of an injectable, or in the form of a food premix, such as mixing with dry meal, mash and the like, and then the prepared premix is added to the regular feed, thereby administering the compound to the domestic or laboratory animal.

The novel therapeutic compounds of the invention can also be formulated into compositions comprising other compounds useful in the sympotomatic therapy of cardiac arrhthmias, epilepsy and other states characterized by involuntary movements such as chorea and Parkinson's syndrome. For example, 3-(N,N-dimethylglycyloxymethyl)diphenylhydantoin methanesulfonate, can be mixed with 5,5-diphenyl-2,4-imidazolidinedione for oral administration at the rate of 200 mg to 600 mg daily, for example, as adminstered in capsule form. Typical capsules comprise 15 mg or 50 mg of 3-(N,N-dimethylglycyloxymethyl)diphenylhydantoin methanesulfonate and 15 mg or 50 mg of 5,5-diphenyl-2,4-imidazolidinedione for oral administration up to 4 times a day.

The novel and useful hydantoates of the invention are adaptable for administration for their physiological antiepileptic and anticonvulsant effects from drug delivery systems, such as skin delivery systems, gastrointestinal drug delivery devices, and the like, wherein the delivery device is manufactured from naturally occurring and synthetic polymeric materials. Representative of materials acceptable for the fabrication of drug delivery systems containing the compounds for controlled drug administration include materials such as polyvinyl chloride, polyisoprene, polybutadiene, polyethylene, ethylene-vinyl acetate copolymers, polydimethylsiloxane, hydrophillic hydrogels of esters of acrylic and methacrylic acid, polyvinyl acetates, propylenevinyl acetate copolymers, and the like.

It is also quite obvious that due to the extremely exceptional solubility characteristics of the claimed compounds over diphenylhydantoin per se and derivatives of the prior art, superior parenteral formulation and administration is achieved. Similarly, improved oral bioavailability is achieved owing to the increased solubility of the subject compounds.

From the foregoing description, it is obvious that one of ordinary skill in the art can easily ascertain the essential characteristics of this invention, and without departing from the spirit and scope thereof, can make various changes and/or modifications to the invention for adapting it to various usages and conditions. As such, these changes and modifications are properly, equitably and intended to be, within the full range of equivalence of the following claims.

What we claim is:

1. A 5,5-diphenylhydantoin compound having the structural formula:

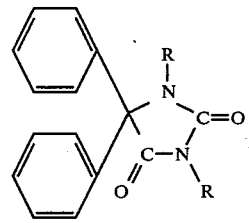

wherein each R is independently selected from the group consisting of hydrogen and —CH($R_1$)—O—P(O)(OH)$_2$, wherein $R_1$ is selected from the group consisting of hydrogen and $C_1$-$C_7$ straight or branched chain alkyl; with the proviso that the R's cannot simultaneously be hydrogen; or the pharmaceutically acceptable acid addition or basic salts, $C_1$-$C_4$ alkylhalide quaternary salts or N-oxide thereof.

2. The compound as defined by claim 1, wherein either R is hydrogen, with the other being —CH($R_1$)—O—P(O)(OH)$_2$.

3. The compound as defined by claim 1, same being 3-phosphoryloxymethyl-5,5-diphenylhydantoin.

* * * * *

UNITED STATES PATENT AND TRADEMARK OFFICE

CERTIFICATE EXTENDING PATENT TERM
UNDER 35 U.S.C. § 156

PATENT NO.     :   4,260,769

ISSUED         :   April 7, 1981

INVENTOR(S)    :   Valentino J. Stella et al.

PATENT OWNER   :   Merck & Co., Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Five years from April 7, 1998, the original expiration date of the patent, with all rights pertaining thereto as provided by 35 U.S.C. § 156(b).

I have caused the seal of the Patent and Trademark Office to be affixed this 15th day of July 1998.

Bruce A. Lehman
Assistant Secretary of Commerce and
Commissioner of Patents and Trademarks